United States Patent
Stephenson et al.

(10) Patent No.: US 6,308,336 B1
(45) Date of Patent: Oct. 30, 2001

(54) HEADGEAR HAVING AIRFLOW CHARACTERISTICS

(76) Inventors: Michael Stephenson, 21615 SW. 187 Ave., Miami, FL (US) 33170; William Dickerson, 2100 College Dr. #137, Baton Rouge, LA (US) 30808

( * ) Notice: Subject to any disclaimer, the term of this patent is extended or adjusted under 35 U.S.C. 154(b) by 8 days.

(21) Appl. No.: 09/717,046

(22) Filed: Nov. 22, 2000

(51) Int. Cl.$^7$ .................................................. A42B 1/24
(52) U.S. Cl. ........................... 2/209.13; 2/10; 2/DIG. 11
(58) Field of Search ........................... 2/10, 12, 13, 6.3, 2/171, 209.13, 209.4, DIG. 11; 351/155

(56) References Cited

U.S. PATENT DOCUMENTS

| | | | |
|---|---|---|---|
| 264,574 | * 9/1882 | Shone | 2/12 |
| 1,832,747 | * 11/1931 | Spoljarich | 2/209.13 |
| 2,874,387 | 2/1959 | Bannister et al. | |
| 3,605,115 | * 9/1971 | Bohner | 2/12 |
| 4,179,753 | * 12/1979 | Aronberg et al. | 2/10 |
| 5,373,583 | * 12/1994 | Birum | 2/10 |
| 5,473,778 | * 12/1995 | Bell | 2/10 |
| 5,487,191 | 1/1996 | Ridley | |
| 5,778,454 | 7/1998 | Oxman | |
| 5,898,935 | 5/1999 | Davis | |
| 5,943,704 | 8/1999 | Oxman | |
| 6,216,282 | * 4/2001 | Marzec | 2/452 |
| 6,237,159 | * 5/2001 | Martin | 2/209.12 |

* cited by examiner

Primary Examiner—John J. Calvert
Assistant Examiner—Katherine Moran
(74) Attorney, Agent, or Firm—Papan Devnani Esq.; C. C. Shroff

(57) ABSTRACT

A visor or cap brim is disclosed that prevents the pressure of the wind from blowing the cap off of the user's head. The visor portion is a generally planar surface that is held out away from the front of the cap portion that sits on the user's head. This creates a single large passage between the visor/bill and the cap and the visor/bill is held at such an angle that it acts a "spoiler" to press the hat down more firmly on the user's head in a high wind while at the same time shading the eyes and forehead from the sun. The visor portion of the cap is removably attached to a semi-rigid headband that encircles the base of the main body of the cap. This attachment is accomplished by either a resilient clip or a mortise taper connection at the terminal ends of a pair of arms attached to the visor portion.

3 Claims, 4 Drawing Sheets

FIG. 7 SECTION A-A

HEADGEAR HAVING AIRFLOW CHARACTERISTICS

BACKGROUND OF THE INVENTION

1. Field of the Invention

The present invention relates generally to headgear. More specifically, it relates to headgear wherein the brim or sunshade portion of the hat is not connected directly to the front portion of the hat proximate the user's forehead, but is only attached at the sides of the hat, i.e. proximate the user's ears. This shading portion of the hat is angled to provide both protection from the sun and to prevent the cap or hat from being dislodged by the wind.

2. Description of the Prior Art

One of the primary disadvantages of current hats or caps is their tendency to be blown off during periods of high wind. The brim of the hat, or the portion designed to protect the user's eyes and forehead from the wind, creates a lifting surface that tends to lift the hat off the head. One of the comic standards of the silent film era is that of the hatless man chasing the errant item of apparel down the street during a windstorm, coming tantalizingly close before nature again blows the hat out of reach.

A common solution to this problem, especially in the case of women's headgear is the hatpin, that attaches the item to the user's hair. In the case of a man's shorter hair, or hair that is not sufficiently thick or piled up on the head, this will not work. Bands or cords that are tied or are elastically connected under the user's chin have also been used to address the problem, as in the case of many "cowboy hats".

The present invention presents a novel solution to this problem, as it shields the eyes and forehead of the user from the sun, but this novel visor or brim is generally planar and a space is left between the body of the cap and the bill/visor The leading and trailing edges of the brim are set at such an angle as to exert force on the cap in a downward direction; i.e. to press the cap more firmly onto the user's head. The angle is set between 25° and 65°, with the optimum angle being 45°.

During a search at the U.S. Patent and Trademark Office, a number of relevant patents were uncovered and they will be discussed below.

First is U.S. Pat. No. 2,874,387 issued to Constance Bannister et al. on Feb. 24, 1959 discloses a visor cap in which a plurality of slats or panels is provided to redirect the flow of air, thus preventing the cap from being blown off by the pressure of the wind. Unlike the present invention, there is no teaching of the brim being substantially completely detached from the front portion of the cap body, creating a large single space or passage to direct the airflow.

Next is U.S. Pat. No. 5,487,191 issued to Robert L. Ridley on Jan. 30, 1996. This discloses a vented visor cap that is unlike the present invention in that the bill or brim of the Ridley cap is clearly attached to the body of the cap itself proximate the front thereof.

In U.S. Pat. No. 5,778,454 issued on Jul. 14, 1998 to Scott E. Oxman there is disclosed a visor cap having a cross-section that, from the front end to the rear end, resembles an inverted airfoil. This, like the Ridley patent above, is dissimilar from the present invention in that there is no teaching of the bill or visor being attached only at the sides of the body of the cap as is seen in the instant invention.

U.S. Pat. No. 5,898,935 issued to Michael B. Davis on May 4, 1999 discloses a cap having an adjustable and interchangeable visor. The novel construction of the visor or brim seen in the instant invention is not seen in this patent.

Lastly, U.S. Pat. No. 5,943,704 issued on Aug. 1, 1999 to Scott E. Oxman, being a divisional case of the '454 patent, above discloses a visor cap. This is an attachment to a visor cap that is itself an airfoil in cross-section. As in all the other patents discussed here, this also does not teach the unique structure of applicant's brim, which is located such that an air space is created between the brim and the cap body.

Thus, while the foregoing overview of prior art indicates it to be well known to modify or shape visor bills or brims to allow air to flow through them, or to be deflected via an airfoil to prevent the hat from being blown off in a high wind, none of the inventions discussed above, either alone or in combination, describe the instant invention as claimed.

SUMMARY OF THE INVENTION

To achieve the foregoing and other advantages, the present invention, briefly described, provides a visor or cap brim that prevents the pressure of the wind from blowing the cap off of the user's head. The visor portion is a generally planar surface that is held out away from the front of the cap portion that sits on the user's head. This creates a single large passage between the visor/bill and the cap and the visor/bill is held at such an angle that it acts a "spoiler" to press the hat down more firmly on the user's head in a high wind while at the same time shading the eyes and forehead from the sun. The visor portion of the cap is removably attached to a semi-rigid headband that encircles the base of the main body of the cap. This attachment is accomplished by either a resilient clip or a mortise taper connection at the terminal ends of a pair of arms attached to the visor portion.

Thus it is a principal object of the invention to provide an article of headgear having airflow characteristics that overcomes the disadvantages of the prior art.

It is a further object of the invention to provide an article of headgear having airflow characteristics wherein the brim or visor portion is a generally planar, rectangular surface.

Still yet a further object of the invention is to provide a an article of headgear having airflow characteristics wherein the visor or brim portion is held in a spaced off relationship is respect to the main body of the cap creating a single air directing channel therebetween.

Yet another object of the invention is to provide a an article of headgear having airflow characteristics that, in the first embodiment of the invention, the brim or visor portion is removably attachable to the main body of the cap through a pair of arms that terminate in resiliently deformable clips that snap into place on the sides of the main body of the cap.

Still yet another object of the invention is to provide an article of headgear having airflow characteristics that, in the second embodiment of the invention, the brim or visor portion of the is removably attachable to the main body of the cap through a similar pair of arms as discussed above, but wherein the arms terminate in a mortise taper connection.

And still yet another object of the invention is to provide an article of headgear having airflow characteristics wherein the alms attaching the brim or visor portion of the cap are attached to a semi-rigid headband portion that encircles the base of the main body of the cap.

These together with still other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and the above objects as well as objects other than those set forth above will become more apparent after a study of the following detailed description thereof. Such description makes reference to the annexed drawings wherein:

FIG. 7 is a cross-sectional view taken along line A—A of FIG. 6.

DESCRIPTION OF THE PREFERRED EMBODIMENTS

Figure 1:
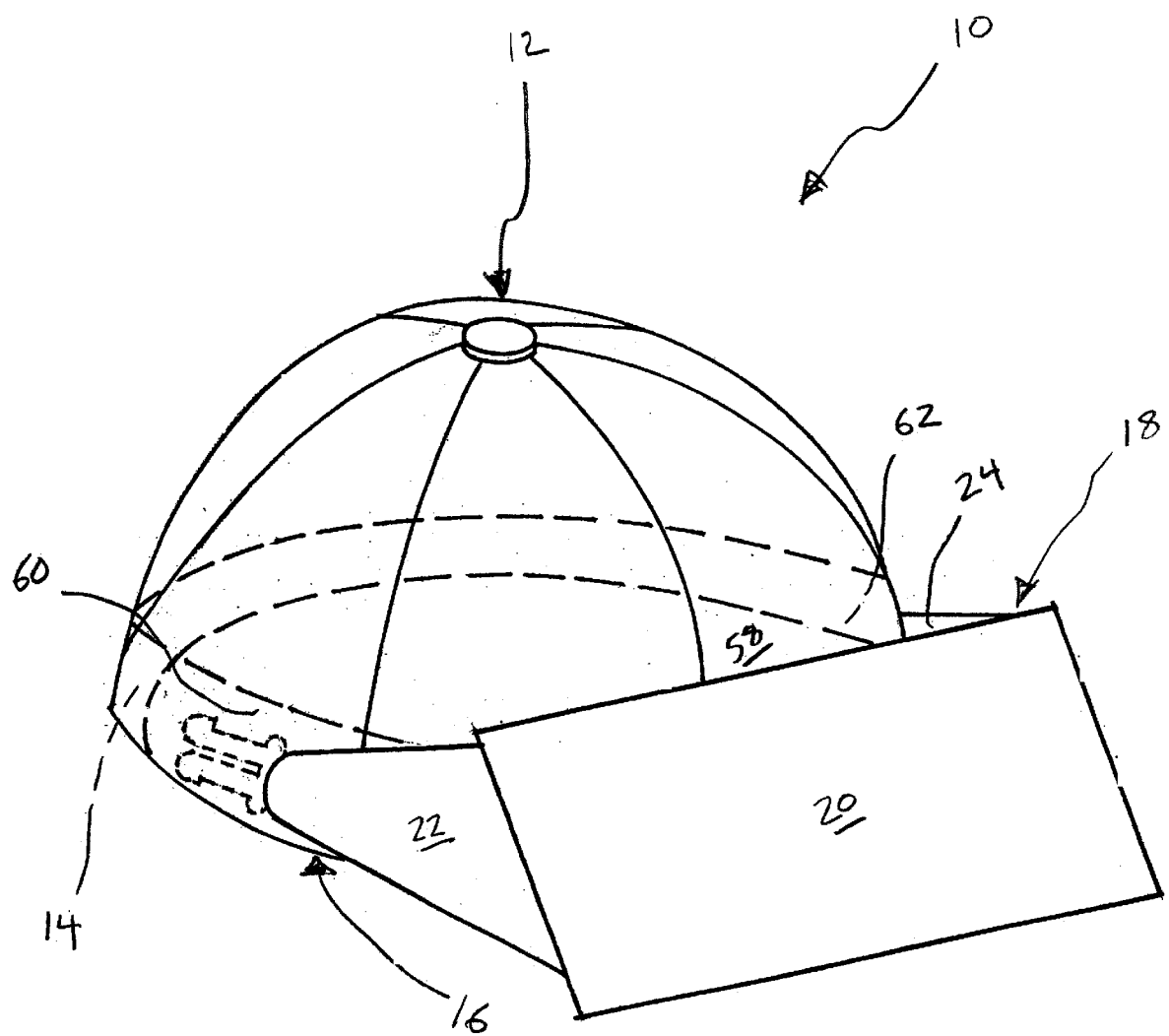
FIG. 1 is a perspective view of the first embodiment of the instant invention.

Referring first to FIGS. 1–4, the first embodiment of the present invention will be discussed. The invention is indicated generally at 10. The main body of the cap 12 is, in the embodiments discussed herein, a dome-shaped cap of the type sometimes referred to as a "beanie". It should be understood at the outset, however, that the shape of this main body portion of the cap does not form part of the inventive structure of the instant invention and that the invention is not limited to this type and many other shapes for headcovering would occur to the skilled practitioner. Included neat the base of the cap body 12 is a semi-rigid headband, shown in FIG. 1 in dotted outline and indicated at 14. This headband 14, which could be made out of any number of suitable materials such as plastic or paper, encircles the base 16 of the main cap body 12.

The discussion, still referring to FIGS. 1–4 now turns to the visor portion of the headgear 10. This visor portion is indicated generally at 18 and includes the main visor portion 20, first arm 22, and second arm 24. Main visor portion 20 is generally planar and is also generally rectangular. It should be noted that many other shapes could be utilized to achieve the same purpose. The main visor portion could be triangular in shape or could be formed into a wide number of polygons that would essentially achieve the same result. The visor portion 18 is made of suitable materials, similar in properties as the semi-rigid headband 14. The visor portion 18 could be made of paper, plastic, or other like material and could be covered by weatherproofing material if desired. Main visor portion 20, by means of the arms 22, 24 is held in a spaced relationship with regard to the cap body 12. This creates the air space 26. The main visor portion 20 is held at angle in relation to the plane of the semi-rigid headband 14. This angle could be anywhere from 25° to 65°, however experimentation has shown that an angle of around 45° is optimal. Additionally, though in the Figures the angle of the main visor portion 20 is shown as being fixed, it could easily be made adjustable in relation to the plane of the semi-rigid headband 14 to allow for varying conditions. Another feature that would occur to skilled practitioner that is not seen in the drawings would be optional apertures in the main visor portion 20.

Figure 2:
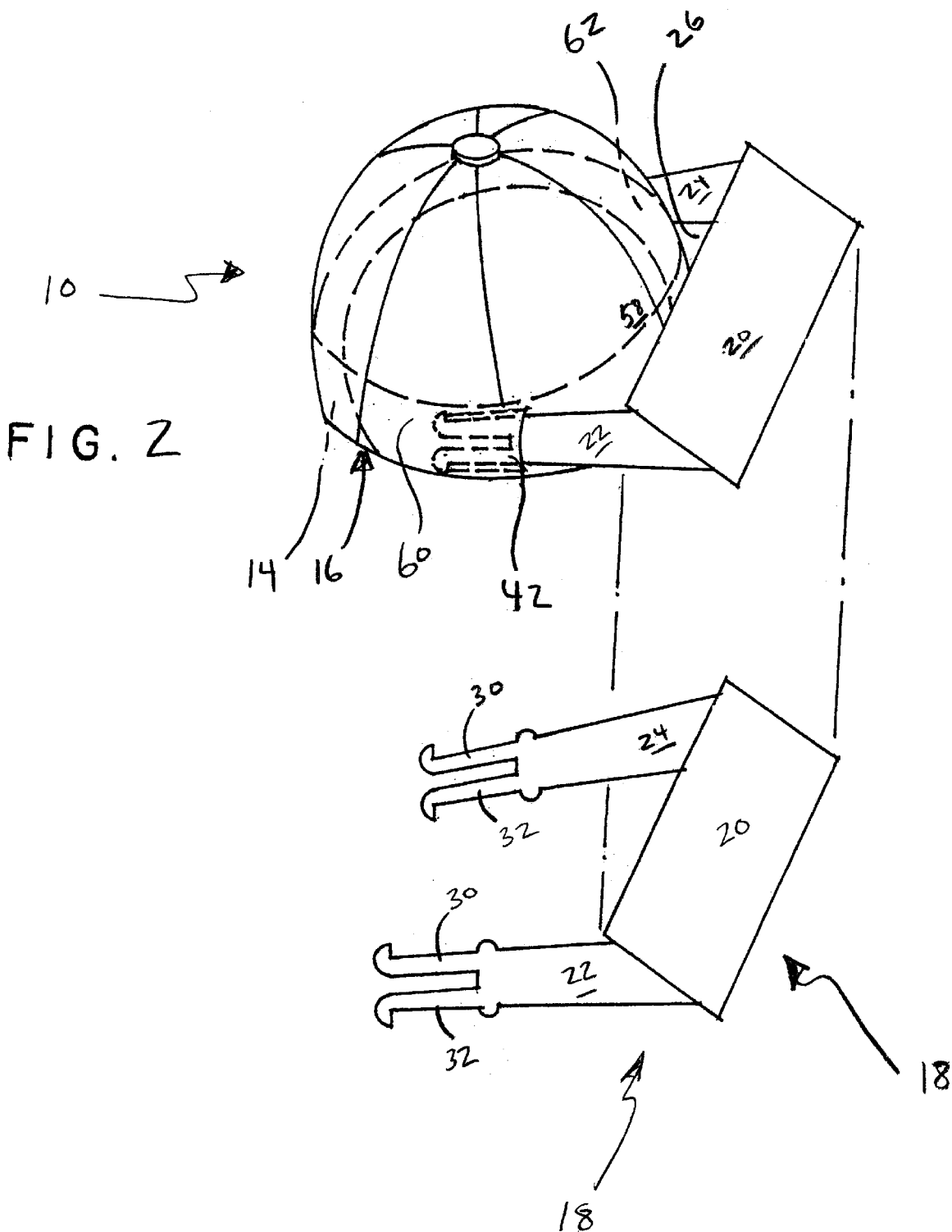
FIG. 2 is a perspective view of the first embodiment of the instant invention showing the visor portion, the pair of arms attached thereto, and the attachment means for connecting same to the semi-rigid headband.
Figure 3:
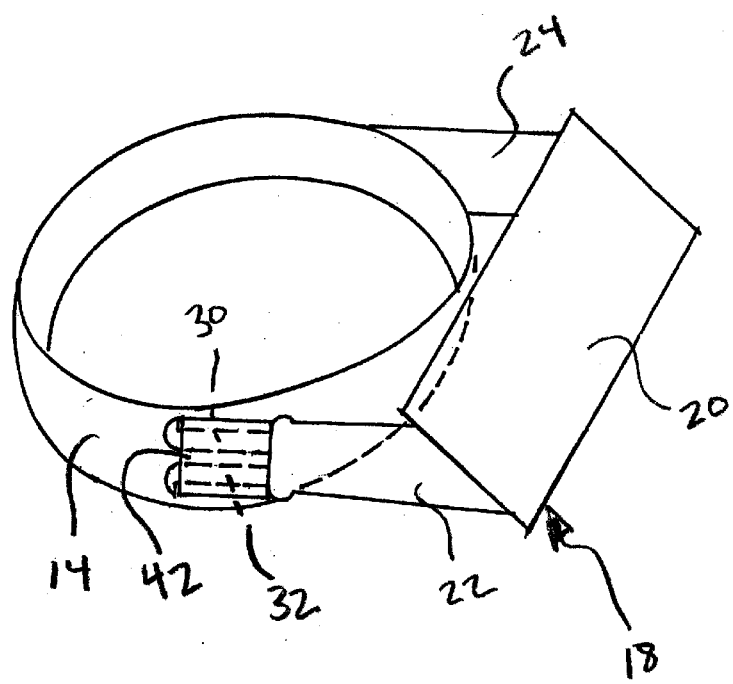
FIG. 3 is a perspective view of the first embodiment of the instant invention, showing only the semi-rigid headband and the attached visor.
Figure 4:
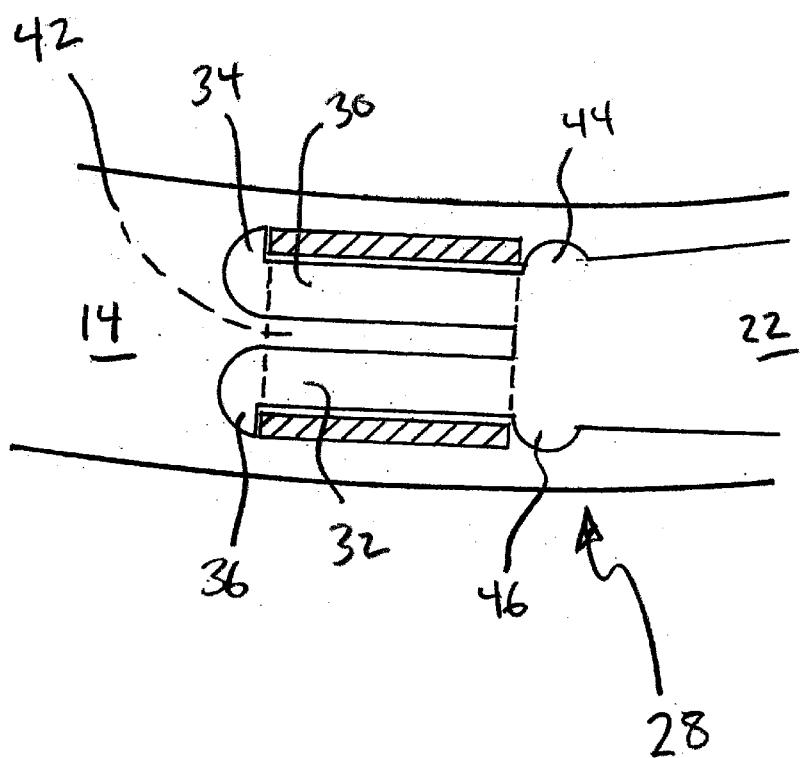
FIG. 4 is a close-up view of the attachment means at the terminal end of one of the arms in the first embodiment of the invention.

The discussion now turns to the attachment means in this first embodiment of the invention. This first attachment means is best seen in FIGS. 3 and 4. At the terminal end 28 of arm 22 there are two resilient clip portions 30, 32. These, in turn, terminate in a pair of hooks or flanges 34, 36 (seen best in FIG. 4). These hooks or flanges 34, 36 clip over protrusions 38, 40 that extend outwardly from the headband 14. The resilient clip portions 30, 32 are thus held fixedly inside pocket 42, which is shown in FIGS. 2, 3, and 4. Secondary flanges 44, 46 on terminal end 28 of arm 22 also assist in keeping the visor portion 18 held in place. It is of course understood that though only arm 22 is shown in the drawings, arm 24 is attached to headband 14 in a generally identical manner.

Figure 5:
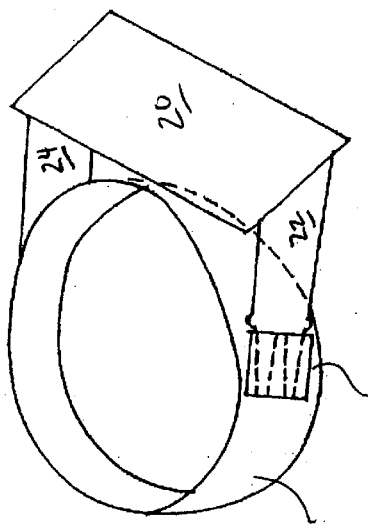
FIG. 5 is a perspective view of the second embodiment of the invention showing the mortise taper attachment means between the terminal ends of the arms and the semi-rigid headband.
Figure 6:
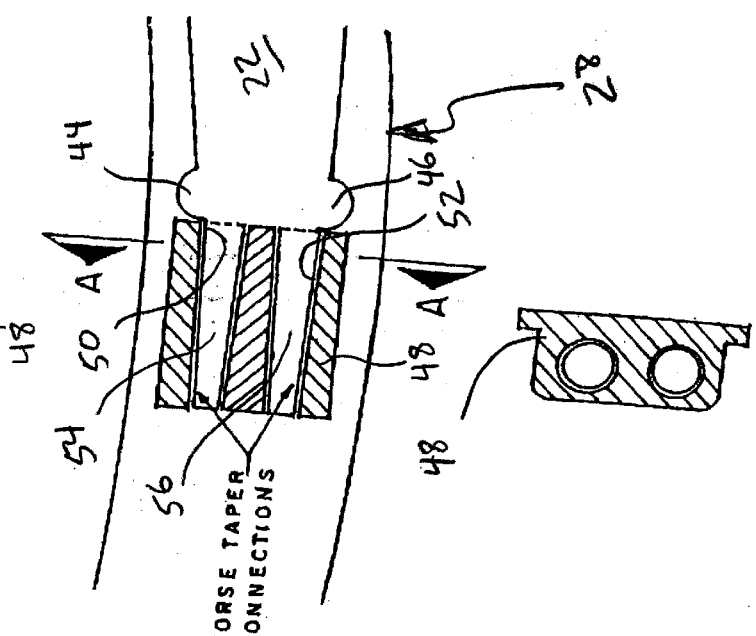
FIG. 6 is a close up view of the terminal end of one of the arms and the mortise taper connection between that end and the semi-rigid headband.

The discussion now turns to the attachment means of the second embodiment of the invention, shown in FIGS. 5–7. In this attachment means, there is no pocket as seen in the first embodiment, but a single protruding portion 48 is provided on the outside of the headband. As seen in FIGS. 6 and 7 two apertures 50, 52 extending therethrough are used to hold extensions 54, 56 frictionally, through what is known as a mortise taper connection. These extensions 54, 56 are, as can be seen, located at the terminal end 28 of arm 22. As in the case of the first embodiment of the invention, arm 22 is also provided with secondary flanges 44, 46 to aid in holding visor portion 18 in place. Also as discussed in the details of the first embodiment, it should be understood that the other arm 24 is attached to the headband 14 in substantially the same manner.

Thus, in operation, when a user is wearing the novel hat or cap 10 and the wind blows, due to the angle of the main visor portion 20, the body 12 of the hat is pressed more firmly onto the user's head and the hat 10 will not fly away. This is accomplished because the main visor portion 20 that shelters the user's eyes and forehead is not attached at the front 58 of the hat body 12. Instead it is only attached at both lateral sides 60, 62, thus leaving, as mentioned above, a single air space 26.

It should be emphasized that the instant invention is not in any way limited to the embodiments as they are described above but encompasses all embodiments as described in the scope of then following claims.

What is claimed as being new and desired to be protected by Letters Patent of the United States is as follows:

1. An article of headgear comprising:
    a main body portion adapted to fit on a users head, said main body portion further includes a semi-rigid headband portion, said semi-rigid headband portion defining a plane on which it generally lies, and where said semi-rigid headband portion also includes two laterally located side portions and a front portion;
    a visor portion having removable attachment means for attaching said visor portion to said main body portion and where said visor portion further includes a main visor body portion, said main visor body portion being generally planar, said visor portion also including;

a pair of arms, each one of said arms having a first end and a second end, each said first end being attached to said main visor body portion and each said second end including said removable attachment means and where said semi-rigid headband portion also includes receiving areas on said laterally located side portions, and where each said arm also extends parallel to said semi-rigid headband between said first end and said second end; whereby said visor portion is attachable to said main body portion of said headgear by said removable attachment means and thereby an airspace is created between said main visor body portion and said front portion of said main body portion, and further where said generally planar main visor body portion is held in a predetermined relationship in relation to said pair of arms, said predetermined relation being an angle between 25 degrees and 65 degrees.

2. The headgear according to claim 1, wherein said removable attachment means comprises a pocket on both of said lateral sides of said semi-rigid headband portions, each said pocket including at least one protrusion, and where said removable attachment means also includes a pair of cooperating resilient clips on each of said terminal arms of said visor portion, said resilient clips including flange means hold said visor portion in a fixed relation with said semi-rigid headband when said resilient clips are inserted into said pocket.

3. The headgear according to claim 1, wherein said removable attachment means includes a pair of apertures located within protrusions on said semi-rigid headbands, said protrusions being located on both of said lateral sides of said semi-rigid headband portions, and where said removable attachment means also includes a pair of extensions located on said terminal ends of each of said arms, said extensions cooperating frictionally with said apertures to hold said visor portion in a fixed relation with said semi-rigid headband when said extensions are inserted into said apertures.

* * * * *